United States Patent [19]

El-Rashidy

[11] Patent Number: 4,889,634
[45] Date of Patent: Dec. 26, 1989

[54] DIALYSATE SOLUTION CONTAINING HYDROXYPROPYL-BETA-CYCLODEXTRIN AND METHOD OF USING SAME

[75] Inventor: Ragab El-Rashidy, Deerfield, Ill.

[73] Assignee: Gynex, Inc., Deerfield, Ill.

[21] Appl. No.: 253,260

[22] Filed: Oct. 4, 1988

[51] Int. Cl.$^4$ .............................................. B01D 13/00
[52] U.S. Cl. ...................................... 210/646; 604/5; 514/58; 252/1
[58] Field of Search ...................... 210/644, 645, 646; 252/1; 604/5; 514/58, 127, 154; 536/103; 106/210

[56] References Cited

U.S. PATENT DOCUMENTS

| | | | |
|---|---|---|---|
| 3,459,731 | 8/1969 | Gramera | 536/103 |
| 3,560,380 | 2/1971 | Stade | 252/1 |
| 4,054,736 | 10/1977 | Hayashi et al. | 536/103 |
| 4,336,881 | 6/1982 | Babb et al. | 252/1 |
| 4,470,975 | 9/1984 | Berger | 536/103 |
| 4,489,535 | 12/1984 | Veltman | 252/1 |
| 4,596,796 | 6/1986 | Pitha | 514/58 |
| 4,727,064 | 2/1988 | Pitha | 514/58 |
| 4,756,838 | 7/1988 | Veltman | 252/1 |

FOREIGN PATENT DOCUMENTS

| | | | |
|---|---|---|---|
| 0955933 | 9/1982 | U.S.S.R. | 604/4 |
| 0000515 | 3/1981 | World Int. Prop. O. | 252/1 |

OTHER PUBLICATIONS

"Beta-Cyclodextrin as an Aid to Peritoneal Dialysis. Renal Toxicity of Beta-Cyclodextrin in the Rat", *Research Communications in Chemical Pathology and Pharmacology* 19 (2): 376 Perrin et al., (Feb. 1978).

"Renal Effects of Parenterally Administered Methylated Cyclodextrin on Rabbits", I. Int. Symposium on Cyclodextrins, Budapest 1981, Serfozo et al., pp. 123–132.

*International Journal of Pharmaceutics* 29 (1986): 73–82.

*Primary Examiner*—Frank Spear
*Assistant Examiner*—Coreen Y. Lee
*Attorney, Agent, or Firm*—Baker & McKenzie

[57] ABSTRACT

A dialysate solution suitable for peritoneal dialysis and containing hydroxypropyl-beta-cyclodextrin is disclosed.

7 Claims, No Drawings

DIALYSATE SOLUTION CONTAINING HYDROXYPROPYL-BETA-CYCLODEXTRIN AND METHOD OF USING SAME

DESCRIPTION

1. Technical Field

This invention relates to a dialysate suitable for peritoneal dialysis as well as for detoxification by hemodialysis, and method of using same.

2. Background Art

Dialysis is most commonly used in the treatment of patients who suffer from kidney loss or kidney malfunction. Dialysis is also effective in the treatment of drug overdoses.

A widely used method of dialysis is extracorporeal hemodialysis. Here the patient's blood is cleansed by passing it through an artificial kidney in an artificial kidney dialysis machine. By the process of diffusion across a semipermeable membrane in the artificial kidney into a dialysate, impurities and toxins, including drugs, are removed from the patient's blood. Water is also removed from the patient's blood by diffusion. This process of removing water is called ultrafiltration.

Hemodialysis is generally required three times a week, each session requiring 4 to 5 hours in a dialysis center or at home. During dialysis, the patient is "tied" to the machine by venous and arterial blood lines which convey the blood to and from the artificial kidney. The activities which the patient can perform are limited while tied to the machine. Thus, the patient's life is seriously affected as his or her daily activities must be planned around these sessions.

Another method of dialysis is peritoneal dialysis. There are two types of such dialysis, intermittent peritoneal dialysis and continuous ambulatory peritoneal dialysis.

With intermittent peritoneal dialysis a dialysate, typically containing glucose as an osmotic agent, is infused into the patient's peritoneal cavity by means of tubing and a catheter. The peritoneum, which defines the peritoneal cavity, is a membrane lining the abdomen and pelvic walls. It contains many small blood vessels and capillary beds which act as a natural semipermeable membrane. This natural membrane may be contrasted with the artificial membrane used in hemodialysis. In both cases impurities, toxins, and water in the blood are removed by diffusion across a membrane, a cellulose membrane of an artificial kidney or a peritoneal membrane of a peritoneal cavity.

The dialysate remains in the patient's peritoneal cavity for a time sufficient for blood waste-products and water to be removed by diffusion across the peritoneal membrane and into the dialysate. The waste-products and water containing dialysate then is drained from the peritoneal cavity by means of a catheter and tubing and a fresh supply of dialysate is infused. Intermittent peritoneal dialysis (IPD) utilizes pumps or other auxilliary equipment to which the patient is "tied" during dialysis. The patient must remain sedentary while "tied" to the equipment. Here also, the patient's activities are seriously impeded.

Continuous ambulatory peritoneal dialysis (CAPD) has the important advantage of enabling the patient to be ambulatory and conduct a normal routine during dialysis. The patient is not "tied" to a machine. The patient need be sedentary only for the time required to drain and infuse dialysate from and into the peritoneal cavity. This infusion and draining is handled by tubing connected to a surgically implanted, indwelling catheter in the patient's abdominal wall in communication with his peritoneal cavity. The patient fills his peritoneal cavity with dialysate, typically the same glucose-containing dialysate used in intermittent peritoneal dialysis, from a collapsible plastic container. When the container is empty, it is not disconnected from the tubing leading into the patient's peritoneal cavity. Instead, the patient simply rolls up or folds the container and tucks it into his clothing. When it is time to drain the solution from his peritoneal cavity, he removes the folded container and drains directly into it. Once full, the patient then replaces the container with a container of fresh dialysate.

Peritoneal dialysates which use glucose as the osmotic agent have several disadvantages, however. One disadvantage is that high glucose concentration in the peritoneal dialysate causes glucose to diffuse through the peritoneum into the bloodstream, providing unwanted caloric input to the patient and causing excessive weight gain (obesity) and elevated triglyceride levels in the patient as well. This absorption of glucose is detrimental to patients with heart disease, lung disease or diabetes.

Another disadvantage is that the diffusion of glucose into the bloodstream reduces the osmolarity, and hence the efficacy, of the peritoneal dialysate. This results in a phenomenon known as "negative ultrafiltration" whereby excess water is *added* to the patient instead of removed from the patient.

Yet another disadvantage is that the glucose in peritoneal dialysates may cause the unwanted loss of amino acids and polypeptides (protein loss) from the bloodstream of the patient.

In addition the pH of the glucose containing peritoneal dialysate (typically in the acidic pH range 5.2–5.5) is not as physiologic as a dialysate having a pH value of 7.4 which some physicians desire. This acidic pH range is required for a glucose-containing dialysate to prevent carmelization of the glucose during sterilization of the dialysate.

A peritoneal dialysate containing beta-cyclodextrin has been reported to accelerate the removal of intravenously administered toxins in rats. However, it was found that high concentrations of beta-cyclodextrin were toxic. See Perrin et al. "Beta-Cyclodextrin As An Aid To Peritoneal Dialysis. Renal Toxicity Of Beta-Cyclodextrin In The Rat," *Research Communications in Chemical Pathology and Pharmacology* 19 (2): 373–376 (Feb. 1978). Similarly, nephrotoxicity has been reported for methylated cyclodextrins. See Serfozo et al., "Renal Effects of Parenterally Administered Methylated Cyclodextrins on Rabbits," *I. Int. Symposium on Cyclodextrins*, Budapest 1981, pp. 123–132.

The present invention, on the other hand, utilizes a different cyclodextrin and provides a dialysate which avoids, or at least minimizes, the aforementioned shortcomings of the prior art.

SUMMARY OF THE INVENTION

The present invention contemplates a glucose-free dialysate. This dialysate utilizes hydroxypropyl-beta-cyclodextrin as the osmotic agent together with the usual physiologically desirable electrolytes. Tests in laboratory animals have shown that the present dialysate performs comparably to a dialysate containing glucose as regards to volume balance and the removal of urea, creatinine, potassium, phosphate and magnesium. A major advantage of the present dialysate is that a negative glucose balance can be achieved during dialysis. This result is beneficial to diabetic patients who require dialysis, patients who are obese, and patients who have high triglyceride and cholesterol levels.

The present invention is also useful in the treatment of drug overdoses by peritoneal as well as hemodialysis inasmuch as a great variety of drugs complex with hydroxypropyl-beta-cyclodextrin and are removed from the bloodstream during dialysis.

DETAILED DESCRIPTION OF THE PREFERRED EMBODIMENTS

While this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

Hydroxypropyl-beta-cyclodextrins are commercially available compounds that are derived from beta-cyclodextrins by condensation with a propylene oxide to provide the corresponding hydroxypropyl derivatives having a degree of substitution (D.S.) up to about 15 or higher. For the purposes of the present invention a D.S. value of about 5 to about 7 is preferred.

The preparation of suitable hydroxypropyl-beta-cyclodextrins is described, inter alia, in International Journal of Pharmaceutics 29 (1986):73-82 and in Journal of Pharmaceutical Sciences 75(6):571-572 (1986). Also known, and contemplated for the purposes of the present invention are the hydroxypropyl-beta-cyclodextrins that are polyethers of cyclodextrins and are obtained by condensation of an excess of hydroxypropylene oxide with beta-cyclodextrin as described in U.S. Pat. No. 3,459,731 to Gzamera et al.

In accordance with this invention, a peritoneal dialysate is provided containing an ion concentration sufficient to cause diffusion of water and toxins across the peritoneum after infusion of the dialysate into the peritoneal cavity of a patient. In addition to a hydroxypropyl-beta-cyclodextrin, the present peritoneal dialysate contains amounts of various physiologically important electrolytes in concentrations comparable to those in normal plasma water. A suitable peritoneal dialysate of the present invention is represented by the following formulation:

hydroxypropyl-beta-cyclodextrin in an amount of about 5 to about 35 g/dl, preferably about 7.5 to about 25 g/dl;
sodium in an amount of about 110 to about 150 mEq/l;
potassium in an amount of about 0 to about 5 mEq/l;
calcium in an amount of about 0 to about 6 mEq/l;
magnesium in an amount of about 0 to about 4 mEq/l; and
alkali equivalent in an amount of about 35 to about 40 mEq/l.

The above constituents and concentrations are merely exemplary, and may be varied in accordance with patient requirements.

Typical dialysate solution compositions are given in Table I. The concentration of each ingredient may vary depending upon the patients' needs, kidney function, and clinical conditions.

TABLE I

Typical Dialysate Solution Compositions

| Ingredient | Formulation 1 | Formulation 2 | Formulation 3 |
|---|---|---|---|
| HPBCD (% W/V) | 7.5 | 15 | 25 |
| Sodium (mEq/l) | 135 | 130 | 120 |
| Potassium (mEq/l) | 3 | 2.5 | 2 |
| Calcium (mEq/l) | 4 | 3.5 | 3 |
| Magnesium (mEq/l) | 1.5 | 1 | 1 |
| Anions[1] | Q.S. | Q.S. | Q.S. |
| pH adjust to | 7.4 | 7.4 | 7.4 |

[1] As lactate, acetate or chloride. The presence of these anions is essential to maintain the acid-base balance of the body. Also, they contribute to achieving the desired osmotic pressure and electrolyte balance.

The present dialysate can be compounded by the following procedure (Formulation 1 per liter):
1. Weigh the exact amount of pyrogen-free hydroxypropyl-beta-cyclodextrin (HPBCD) (75 grams), and dissolve in approximately 700 milliliters of deionized water for injection.
2. Weigh the exact amount of sodium (135 milliequivalent), potassium (3 milliequivalent), calcium (4 milliequivalent) and magnesium (1.5 milliequivalent) salts, and add to the solution prepared in step #1.
3. Adjust the pH to 7.4 by the addition of 1 normal HCl or 1 normal NaOH. Also, measure and adjust, if needed, the osmolality using an osmometer. Adjust the final volume to one liter by adding deionized water for injection.
4. The final solution is then sterilized by filtration, using about a 0.22 micron filter, or other appropriate sterilization methods.
5. In a sterile environment, the solution is then put into sterile containers.
6. Microbiol and sterility tests are then performed according to United States Pharmacopeia (U.S.P.) procedures.
7. Particulate matters are then analyzed according to U.S.P. requirements.

The present dialysate is utilized by introducing an aliquot of the dialysate into the peritoneal cavity of a patient in need of dialysis, maintaining the introduced dialysate in the peritoneal cavity for a time period sufficient for toxins to enter the dialysate, usually for a time period of about 2 to about 8 hours, and thereafter removing from the peritoneal cavity a dialysate aliquot having an increased toxin content.

A study was conducted to compare glucose and hydroxypropyl-beta-cyclodextrin (HPBCD) as osmotic agents in peritoneal dialysates.

The two solutions used in this study were: (1) a commercial, standard peritoneal dialysis solution (SPDS) containing 1.5 wt.-% glucose and having a pH of about 5.2 to 5.4, (Dianeal ® Peritoneal Dialysis Solution, Baxter Laboratories) as reference, and (2) an equi-osmolar solution of HPBCD (7.5% W/V) that was substantially the same as the commercial 1.5 wt.-% glucose solution except for HPBCD replacing glucose.

The composition of Dianeal ® is as follows (per liter): sodium chloride, 567.0 mg; calcium chloride, 22.1 mg; magnesium chloride, 15.2 mg; sodium acetate, 392.0 mg; and glucose, 15,000 mg. The osmolality is 347 milliosmoles per kilogram (mOsm/kg), and the pH is 5.2 to 5.4.

The study involved evaluation of HPBCD instilled intraperitoneally as an effective agent for removal of uremic toxins. The elements of the study involved:
 a. Solutions: Two different solutions were utilized:

1. SPDS containing 1.5 weight percent glucose.
2. SPDS where the glucose is replaced by 7.5 weight percent HPBCD.

Solution 2 shows that HPBCD can replace glucose as an osmotic agent in peritoneal dialysis.

b. Animal model: Uremia was induced in adult rats weighing 350 to 400 grams by complete right nephrectomy and partial cryoinfarction of 60 to 80% of the left kidney. The uremia was induced by a two step surgical procedure under anesthesia. The peritoneal dialysis was done one week after the induction of uremia to allow for the development of full uremic toxicity and accumulation of waste products. It is usual for rats prepared in this fashion to have blood urea nitrogen (BUN) levels of between 120 to 140 mg/dl. Rats with this BUN level will survive for several weeks, long enough to perform the intended acute studies. Ten rats were allocated to each group, but 25 rats were prepared to allow for possible loss due to experimental accidents or unexpected developments.

c. Dialysis procedure: Rats were anesthetized by inactin, a long acting barbiturate, and placed on heating pads to maintain body temperature at normal levels. A tracheostomy was performed and one carotid artery was cannulated with a PE 50 catheter to allow blood sampling. A PE 90 catheter was introduced percutaneously into the peritoneal cavity through an 18 gauge needle inserted in the midline of the abdomen. The needle was removed and the catheter connected to a syringe containing the dialysate solution. Half an hour after the end of surgery, 2 ml of blood were withdrawn through the carotid catheter, the plasma separated by centrifugation and the red blood cells (RBC) reinfused. The plasma was used to measure predialysis BUN, creatinine, Na, K, osmolarity and phosphate. After reinfusion of the RBC, dialysate warmed to 37° C. was instilled in the abdominal cavity via the PE 90 catheter at a volume of 10 ml/100 grams body weight. The dwell time was two hours. One hour after instillation of the peritoneal dialysate, 2 ml of blood were withdrawn through the carotid catheter, the plasma separated by centrifugation and the RBC reinfused. At the end of the dwell time, the dialysate was removed, its volume measured and the solution saved for performance of the following measurements: BUN, creatinine, Na, K, osmolarity, phosphate and total protein. After the dialysate was removed, a blood sample was obtained through the carotid catheter for the same measurements done on predialysis and middle dialysis plasma samples.

d. Calculations: The measurements performed allowed calculation of clearance of small molecules such as BUN, middle molecule such as creatinine, and changes in electrolytes, and protein loss into the peritoneal fluid. These measurements also allowed evaluation of the ultrafiltration rate and the fluid removal.

The results are set forth in Table II, below.

TABLE II

Results of Comparative Dialysis
(mean ± st.dev, n = 5)

| | Dialysate | |
|---|---|---|
| | Glucose | HPBCD |
| Volume in | | |
| Absolute (ml) | 43.8 ± 8.6 | 40.6 ± 7.5 |
| Per body weight (ml/100 g) | 14.2 ± 1.4 | 14.6 ± 0-2 |
| Volume out | | |
| Absolute (ml) | 39.4 ± 3.5 | 39.4 ± 2.4 |
| Per body weight (ml/100 g) | 13.2 ± 1.5 | 13.9 ± 0.4 |
| Urea removal | | |
| Pre-BUN[1] (mg/dl) | 144 ± 9 | 134 ± 11 |
| Post-BUN (mg/dl) | 124 ± 13 | 125 ± 16 |
| Urea removed | | |
| Absolute (mg) | 46 ± 12 | 42 ± 5 |
| Per ml (mg/ml) | 1.1 ± 0.2 | 1.1 ± 0.1 |
| Creatinine removal | | |
| Pre-creatinine (mg/dl) | 3.9 ± 0.1 | 3.9 ± 0-4 |
| Post-creatinine (mg/dl) | 3.3 ± 0.7 | 3.3 ± 0.4 |
| Creatinine removed | | |
| Absolute (mg) | 1.1 ± 0.3 | 0.99 ± 0.1 |
| Per ml (g) | 27.4 ± 4.6 | 25.2 ± 3.6 |
| Removal of other compounds | | |
| Potassium (Eq) | 154 ± 71 | 183 ± 43 |
| Phosphate (mg) | 2.7 ± 1.1 | 2.6 ± 0.3 |
| Magnesium (g) | 166 ± 158 | 180 ± 107 |
| Uric acid (mg/dl) range | 0.2 to 0.4 | 0.2 to 0.7 |
| Glucose balance | (negative values reflect removal of glucose from animal) | |
| Glucose in dialysate (mg/dl) | | |
| Pre-dialysis | 1500 | 0 |
| Post-dialysis | 548 ± 162 | 114 ± 28 |
| Glucose balance (mg) | 428 ± 94 | −45 ± 11 |

[1]Blood urea nitrogen

As can be seen, the performance of the glucose dialysate is comparable to the HPBCD dialysate in the removal of undesirable constituents. However, the clear superiority of the HPBCD dialysate over the glucose dialysate can be readily appreciated when the glucose balance is analyzed. The HPBCD dialysate actually reduces the level of glucose in the bloodstream! In contradistinction, the glucose dialysate increases the glucose in the bloodstream which, as previously mentioned, is detrimental as this provides unwanted glucose calories, adversely affects patients with heart disease, lung disease, obesity or diabetes. Also, diffusion of glucose to the bloodstream reduces the osmolarity, and hence the efficacity, of the dialysate necessitating more volume of dialysate per day. While uric acid results are not conclusive, the higher uric acid concentration in HPBCD dialysate suggests higher removal capacity for this solution than for glucose.

Reports in literature, including the previously mentioned Perrin, et al. report, have shown beta-cyclodextrin (BCD) to be toxic to laboratory animals. The use of BCD results in an enlargement of the kidneys and death due to kidney failure (i.e., BCD is nephrotoxic).

A first study was conducted to determine the relative nephrotoxicity of HPBCD and BCD. A control group using phosphate buffer solution was also included in the study.

Three groups of normal rats were utilized in this study. The solutions, which were administered intraperitoneally, all had a pH of 7.4, a temperature of 37° C. and were instilled at a dosage of 15 ml/100 g body weight. Group I rats were given the vehicle solution of phosphate buffer saline (PBS). Group II rats were subdivided into three sub-groups. The first sub-group received a solution having a concentration of 1.5% HPBCD, the second sub-group received a solution having a concentration of 3% HPBCD while the third sub-group received a solution having a concentration of 6% HPBCD. Group III rats were given a solution having a concentration of 0.75% BCD.

Animals from each group were sacrificed at 24 and 72 hours after injection of the peritoneal solution. The animals were sacrificed under general anesthesia and exsanguinated from the abdominal aorta. Plasma was separated and blood urea nitrogen and creatinine was measured and used as an index of renal toxicity of the solutions.

The results of the study are presented in TABLES III, and IV below:

TABLE III
Summary of Nephrotoxicity Results

| Parameter | Control Group Phoshate Buffer 1 and 3 day | BCD Group[1] 1 day | BCD Group[1] 3 day | HPBCD Group 1 day[2] | HPBCD Group 3 day[3] |
|---|---|---|---|---|---|
| Mortality (died/total) | 0/6 | 1/6 | 8/9 | 0/6 | 0/6 |
| Kidney size | normal | enlarged | enlarged | normal | normal |
| Kidney weight | normal | increased | increased | normal | normal |
| BUN (mg/dl) | 15.5[4] | 79.4 | animals died | 14.8 | 19.8 |
| Conclusion | no kidney damage | kidney failure | kidney failure | no kidney damage | no kidney damage |

[1] 0.75% w/v solution. 15 ml/100 g body weight.
[2] Both 1.5 and 3% w/v solutions were used for the 1 day group. 15 ml/100 g body weight.
[3] Both 1.5 and 3% w/v solutions were used for the 3 day group. 15 ml/100 g body weight.
[4] Normal BUN eight times that of the concentration of BCD in the BCD solutions.

As part of the toxicological evaluation of HPBCD, control groups of animals were dosed with HPBCD alone. The results of the studies relating to HPBCD and a saline control are described below.

(a) Studies in rats

Two groups (5/sex/group) of rats [Crl:CD(SD) BR strain] were used for this study. Control rats were given 200 mg of salt per kilogram of body weight intravenously administered in a saline control solution comprising 20% salt by weight in water. The saline control was administered every second day for 14 days (i.e. seven injections). The treated rats were given 200 mg of HPBCD per kilogram of body weight intravenously administered (200 mg/kg i.v. HPBCD) via a HPBCD solution containing 20% HPBCD by weight in water on the same injection schedule. Animals were observed for signs of toxicity. At the end of the study the animals were necropsied, gross pathology was observed, histopathological samples were prepared and blood was drawn for clinical laboratory measurements.

TABLE V
Antemortem Observations For Rats Treated Intravenously Every Second Day For 14 Days With Saline Control or HPBCD Solution.

| Group | Number of deaths | Number of observations |
|---|---|---|
| Male-saline control | 0/5 | 0/5 |
| Male-HPBCD | 0/5 | 1/5, bloody crust[1] |
| Female-saline control | 0/5 | 0/5 |
| Female-HPBCD | 0/5 | 0/5 |

[1] Unrelated to treatment.

TABLE IV
Summary of Nephrotoxicity Results

| GROUP | Wt (i) g | Wt (f) g | Rt kd mg | Rt kd/wt mg/g | Lt kd mg | Lt kd/wt mg/g | BUN mg/dL | Mortality % |
|---|---|---|---|---|---|---|---|---|
| CONTROL 1d (n = 6) | 216 15.4* | 213 13 | 809 0 | 3.78 0.14 | 813 70 | 3.8 0.16 | 15.5 3.8 | 0 |
| HPBCD 1d (n = 6) 1.5% | 213 17.3* | 210 15.8 | 860 86 | 4.08 0.29 | 867 84 | 4.11 0.22 | 14.8 2.9 | 0 |
| HPBCD 1d (n = 6) 3% | 322 19.6* | 301 16.1 | 1054 50 | 3.49 0.12 | 1034 48 | 3.43 0.19 | 15.7 2.2 | 0 |
| HPBCD 1d (n = 6) 6% | 240 4.47* | 227 7.4 | 1066 59 | 4.70 0.14 | 1076 114 | 4.73 0.4 | 14.5 3.48 | 0 |
| BCD 1d (n = 6) 0.75% | 223 10.2* | 218 9.1 | 1307 152 | 5.98 0.82 | 1272 153 | 5.83 0.88 | 79.4 22.7 | 16.67 |
| CONTROL 3d (n = 7) | 271 41.3* | 259 40.5 | 991 138 | 3.84 0.3 | 960 146 | 3.71 0.32 | 17.7 3.8 | 0 |
| HPBCD 3d (n = 6) 1.5% | 296 34.1* | 280 27.5 | 1009 90 | 3.61 0.26 | 1027 74 | 3.68 0.32 | 19.8 2.7 | 0 |
| HPBCD 3d (n = 6) 3% | 275 26* | 267 22.7 | 1009 89 | 3.78 0.25 | 995 88 | 3.72 0.19 | 19.9 3.77 | 0 |
| BCD 3d (n = 9) 0.75% | — | — | — | — | — | — | — | 77.78 |

Wt (i) = initial body weight
Wt (f) = final body weight, i.e., at time of sacrifice
Rt kd = Right kidney
Lt kd = Left kidney
wt = Body weight
BUN = Blood Urea Nitrogen
Control = Phosphate buffer solution
HPBCD = Hydroxypropyl-beta-cyclodextrin; D.S. = about 5
1d = 1 day
3d = 3 day
n = Number of animals
* = Standard deviation
BCD = Beta-cyclodextrin One rat in the BCD 1d Group and all but two of the nine rats in the BCD 3rd Group died of kidney failure. None of the rats in the HPBCD or Control Groups died, notwithstanding the fact that the concentration of HPBCD in the HPBCD solutions was two, four or

TABLE VI

Body Weight Gain (In Grams) For Rats Treated Intravenously Every Second Day For 14 Days With Saline Control or HPBCD Solution.

| | Saline Control | HPBCD |
|---|---|---|
| Male | week 1 36.8 ± 5.28 | week 1 45.7 ± 4.69 |
| | week 2 36.6 ± 5.00 | week 2 41.7 ± 5.20 |
| Female | week 1 16.8 ± 6.55 | week 1 16.0 ± 5.00 |
| | week 2 19.9 ± 4.38 | week 2 18.0 ± 4.21 |

No difference in body weight gains between the saline control and HPBCD solution treated groups was observed.

TABLE VII

Food Intake (In Grams) For Rats Treated Saline Intravenously Every Second Day For 14 Days With Saline Control or HPBCD Solution.

| | | Saline Control | | HPBCD |
|---|---|---|---|---|
| Male | week 1 | 152.3 ± 8.06 | week 1 | 144.8 ± 7.77 |
| | week 2 | 151.5 ± 10.78 | week 2 | 151.1 ± 5 22 |
| Female | week 1 | 97.8 ± 12.50 | week 1 | 107.9 ± 10.59 |
| | week 2 | 106.4 ± 9.51 | week 2 | 112.1 ± 12.47 |

No difference in food intake between the saline control and HPBCD solution treated groups was observed.

TABLE VIII

Hematology Results For Pre-Study Control Male Rats And Those Given a Saline Control or HPBCD Solution Intravenously Every 2 Days For 14 Days.

| Blood component | Pre-study control | Saline control | HPBCD |
|---|---|---|---|
| Red blood cell ($\times 10^6/mm^3$) | 6.48 ± 0.27 | 8.02 ± 0.19 | 7.55 ± 0.17 |
| Hemoglobin (G/DL) | 13.1 ± 0.59 | 15.6 ± 0.41 | 14.6 ± 0.51 |
| Hematocrit (%) | 44.8 ± 1.86 | 50.9 ± 0.73 | 48.6 ± 1.74 |
| Mean corpuscle (FL) | 69.0 ± 1.10 | 63.0 ± 1.10 | 64.0 ± 2.20 |
| Mean corpuscle hemoglobin (pg) | 20.2 ± 0.67 | 19.5 ± 0.09 | 19.3 ± 0.60 |
| Mean corpuscle hemoglobin concentrative (%) | 29.2 ± 0.87 | 30.6 ± 0.51 | 30.0 ± 0.35 |
| Platelet count ($\times 10^3/mm^3$) | 1111.8 ± 133.6 | 949.0 ± 55.9 | 1020.0 ± 79.5 |
| Normal blood cells (/100 white blood cells) | 0 ± 0.3 | 0 ± 0.4 | 0 ± 0.0 |
| White blood cells ($\times 10^3/mm^3$) | 7.5 ± 1.79 | 8.7 ± 2.23 | 7.9 ± 1.18 |
| Segmented neutrophils ($\times 10^3/mm^3$) | 0.65 ± 0.48 | 0.67 ± 0.29 | 0.61 ± 0.44 |
| Lymphocytes ($\times 10^3/mm^3$) | 6.64 ± 1.43 | 7.85 ± 2.08 | 7.13 ± 1.08 |
| Monocytes ($\times 10^3/mm^3$) | 0.16 ± 0.13 | 0.12 ± 0.23 | 0.08 ± 0.01 |
| Eosinophils ($\times 10^3/mm^3$) | 0.01 ± 0.00 | 0.02 ± 0.05 | 0.07 ± 0.05 |
| Basophils ($\times 10^3/mm^3$) | 0.00 ± 0.00 | 0.00 ± 0.00 | 0.00 ± 0.00 |

TABLE IX

Hematology Results For Pre-Study Control Female Rats And Those Given a Saline Control or HPBCD Solution Intravenously Every 2 Days For 14 Days.

| Blood component | Pre-study control | Saline control | HPBCD |
|---|---|---|---|
| Red blood cell ($\times 10^6/mm^3$) | 6.75 ± 0.19 | 7.67 ± 0.41 | 7.32 ± 1.00 |
| Hemoglobin (G/DL) | 13.2 ± 0.46 | 14.8 ± 0.80 | 13.6 ± 3.06 |
| Hematocrit (%) | 46.1 ± 1.39 | 49.2 ± 2.63 | 47.2 ± 5.59 |
| Mean corpuscle (FL) | 68.0 ± 1.30 | 64.0 ± 1.50 | 65.0 ± 2.70 |
| Mean corpuscle hemoglobin (pg) | 19.6 ± 0.56 | 19.3 ± 0.50 | 18.4 ± 2.41 |
| Mean corpuscle hemoglobin concentrative (%) | 28.7 ± 0.25 | 30.0 ± 0.33 | 28.6 ± 3.75 |
| Platelet count ($\times 10^3/mm^3$) | 1142 ± 99.60 | 1105 ± 114.60 | 924 ± 395.20 |
| Normal blood cells (/100 white blood cells) | 0.0 ± 0.40 | 0.0 ± 0.00 | 0.0 ± 0.00 |
| White blood cells ($\times 10^3/mm^3$) | 6.0 ± 1.78 | 5.1 ± 0.82 | 7.4 ± 2.56 |
| Segmented neutophils ($\times 10^3/mm^3$) | 0.42 ± 0.20 | 0.80 ± 0.28 | 0.49 ± 0.22 |
| Lymphocytes ($\times 10^3/mm^3$) | 5.54 ± 1.76 | 4.23 ± 0.68 | 6.80 ± 2.42 |
| Monocytes ($\times 10^3/mm^3$) | 0.02 ± 0.03 | 0.05 ± 0.04 | 0.05 ± 0.08 |
| Eosinophils ($\times 10^3/mm^3$) | 0.00 ± 0.02 | 0.03 ± 0.03 | 0.06 ± 0.04 |
| Basophils ($\times 10^3/mm^3$) | 0.00 ± 0.00 | 0.00 ± 0.00 | 0.00 ± 0.00 |

TABLE X

Blood Chemistry Values For Pre-Study Control Male Rats And Those Given a Saline Control or HPBCD Solution Intravenously Every 2 Days For 14 Days.

| Blood component | Pre-study control | Saline control | HPBCD |
|---|---|---|---|
| Glucose (mg/dL) | 76.6 ± 11.1 | 107.5 ± 16.91 | 94.1 ± 7.43 |
| Total proteins (G/dL) | 5.7 ± 0.18 | 6.3 ± 0.34 | 6.3 ± 0.18 |
| Albumin (G/dL) | 3.1 ± 0.12 | 3.0 ± 0.12 | 3.0 ± 0.08 |
| Globulin (G/dL) | 2.6 ± 0.15 | 3.3 ± 0.26 | 3.3 ± 0.20 |
| Abumin/Globulin (Ratio) | 1.2 ± 0.07 | 0.9 ± 0.04 | 0.9 ± 0.08 |
| Total bilirubin (mg/dL) | 0.3 ± 0.06 | 0.3 ± 0.07 | 0.2 ± 0.04 |
| Cholesterol (mg/dL) | 75.0 ± 9.00 | 36.0 ± 15.60 | 33.0 ± 7.10 |
| Triglycerides (mg/dL) | 106.0 ± 46.20 | 56.0 ± 34.00 | 57.0 ± 17.10 |
| Aspartate amino transferase (IU/L) | 108.0 ± 11.80 | 109.0 ± 32.50 | 124.0 ± 37.36 |
| Alanine amino transferase (IU/L) | 29.0 ± 3.10 | 22.0 ± 4.10 | 24.0 ± 6.70 |
| Alkaline phosphatase (IU/L) | 218.0 ± 51.60 | 127.0 ± 15.00 | 137.0 ± 26.20 |
| Blood urea nitrogen (mg/dL) | 11.2 ± 2.97 | 11.2 ± 1.10 | 11.2 ± 0.87 |
| Creatinine (mg/dL) | 0.8 ± 0.07 | 0.8 ± 0.04 | 0.8 ± 0.04 |
| Calcium (mg/dL) | 9.1 ± 0.81 | 10.0 ± 0.38 | 9.8 ± 0.31 |
| Ionic phosphate (mg/dL) | 10.9 ± 0.60 | 9.4 ± 0.72 | 9.7 ± 0.34 |
| Sodium (mmol/dL) | 139.0 ± 1.00 | 142.0 ± 1.20 | 142.0 ± 1.50 |
| Potassium (mmol/L) | 4.7 ± 0.42 | 4.4 ± 0.25 | 4.7 ± 0.15 |
| Chlorine (mmol/L) | 106.0 ± 1.30 | 105.0 ± 3.80 | 106.0 ± 1.80 |

TABLE XI

Blood Chemistry Values For pre-Study Control Female Rats And Those Given Saline Contol or HPBCD Solution Intravenously Every 2 Days For 14 Days.

| Blood component | Pre-study control | Saline control | HPBCD |
|---|---|---|---|
| Glucose (mg/dL) | 86.0 ± 9.35 | 102.9 ± 11.52 | 100.0 ± 14.07 |
| Total proteins (G/dL) | 5.7 ± 0.25 | 6.5 ± 0.05 | 6.5 ± 0.38 |
| Albumin (G/dL) | 3.3 ± 0.12 | 3.2 ± 0.11 | 3.1 ± 0.08 |
| Globulin (G/dL) | 2.5 ± 0.17 | 3.3 ± 0.11 | 3.4 ± 0.26 |
| Albumin/Globulin (Ratio) | 1.4 ± 0.08 | 1.0 ± 0.08 | 0.9 ± 0.06 |
| Total bilirubin (mg/dL) | 0.3 ± 0.06 | 0.3 ± 0.05 | 0.3 ± 0.05 |
| Cholesterol (mg/dL) | 74.0 ± 9.00 | 48.0 ± 11.70 | 52.0 ± 18.60 |
| Triglycerides (mg/dL) | 78.0 ± 22.90 | 41.0 ± 11.40 | 35.0 ± 12.00 |
| Aspartate amino transferase (IU/L) | 115.0 ± 25.50 | 102.0 ± 24.30 | 102.0 ± 162.00 |
| Alanine amino transferase (IU/L) | 24.0 ± 3.20 | 19.0 ± 2.70 | 21.0 ± 2.30 |
| Alkaline phosphatase (IU/L) | 169.0 ± 51.00 | 100.0 ± 18.40 | 109.0 ± 16.20 |
| Blood urea nitrogen (mg/dL) | 11.7 ± 2.43 | 11.5 ± 0.43 | 13.2 ± 2.52 |
| Creatinine (mg/dL) | 0.6 ± 0.08 | 0.8 ± 0.08 | 0.8 ± 0.11 |
| Calcium (mg/dL) | 9.2 ± 0.81 | 9.9 ± 0.29 | 10.1 ± 0.82 |
| Ionic phosphate (mg/dL) | 105.0 ± 0.49 | 8.3 ± 0.88 | 8.3 ± 0.82 |
| Sodium (mmol/L) | 142.0 ± 1.80 | 142.0 ± 0.80 | 141.0 ± 1.10 |
| Potassium (mmol/L) | 4.8 ± 0.54 | 4.5 ± 0.38 | 4.5 ± 0.16 |
| Chlorine | 111.0 ± 3.00 | 108.0 ± 1.50 | 107.0 ± 2.60 |

There were no observed clinically significant differences in clinical laboratory values between a pre-study control group, the saline control group and the HPBCD treated group (TABLES VIII to XI).

TABLE XII

Organ Weight to Total Body Weight Ratios Expressed as Weight Percent of Total Body Weight.

| Organ | Males Saline Control | Males HPBCD | Females Saline Control | Females HPBCD |
|---|---|---|---|---|
| Brain | 0.7231 | 0.7153 | 1.0628 | 1.0589 |
| Heart | 0.3656 | 0.3787 | 0.4094 | 0.4079 |
| Liver | 3.0370 | 3.0391 | 3.3634 | 3.5723 |
| Kidney | 0.8923 | 0.9022 | 0.8810 | 0.9937 |
| Adrenals | 0.0200 | 0.0212 | 0.0367 | 0.0328 |
| Salivary glands | 0.2311 | 0.2301 | 0.2546 | 0.2701 |
| Spleen | 0.2000 | 0.1943 | 0.1885 | 0.2246 |
| Thymus | 0.2555 | 0.2089 | 0.2886 | 0.2904 |
| Thyroid | 0.0071 | 0.0078 | 0.0083 | 0.0058 |
| Testes | 1.0423 | 1.0209 | — | — |
| Prostate | 0.2085 | 0.2091 | — | — |
| Epididymes | 0.2658 | 0.2635 | — | — |
| Ovaries | — | — | 0.0611 | 0.0574 |
| Uterus | — | — | 0.2574 | 0.3278 |
| Pituitary | 0.0046 | 0.0048 | 0.0064 | 0.0066 |

No changes in gross pathology attributable to HPBCD treatment were observed and organ to body ratios were not different between the groups (TABLE XII).

It is concluded that a regimen of 200 mg/kg i.v. of HPBCD administered every 2 days for 14 days to rats is without toxicological effects.

(b) Studies in monkeys

Two groups (1/sex/group) of Cynomolgus monkeys were used for this study. Control monkeys were given 200 mg of salt per kilogram of body weight intravenously administered as a saline control solution of 20% by weight in water. The saline control was administered every second day for 14 days (i.e. 7 doses). The treated monkeys were given 200 mg/kg i.v. HPBCD on the same injection schedule. Animals were observed for signs of toxicity. At the end of the study the animals were necropsied, gross pathology was observed, histopathology samples were prepared and blood was drawn for clinical laboratory measurements.

TABLE XIII

Individual Body Weight Data, in Kilograms

| Group | Initiation | Study Week 1 | Study Week 2 |
|---|---|---|---|
| Males | | | |
| Group 1 - saline control | 3.14 | 3.15 | 3.17 |
| Group 2 - HPBCD | 2.86 | 2.81 | 2.88 |
| Females | | | |
| Group 1 - saline control | 2.77 | 2.80 | 2.78 |
| Group 2 - HPBCD | 2.73 | 2.74 | 2.74 |

TABLE XIV

Summary of Daily Food Consumption Data, in Grams

| Group | Study Week −2 | −1 | 1 | 2 |
|---|---|---|---|---|
| Males | | | | |
| Group 1 - saline control | | | | |
| Mean | 154.7 | 151.4 | 148.0 | 166.1 |
| Standard deviation | 23.61 | 39.23 | 27.62 | 5.37 |
| $N^1$ | 7 | 7 | 7 | 7 |
| Group 2 - HPBCD | | | | |
| Mean | 170.0 | 166.9 | 161.1 | 171.9 |
| Standard deviation | 10.30 | 16.38 | 14.25 | 15.14 |
| $N^1$ | 7 | 7 | 7 | 7 |
| Females | | | | |
| Group 1 - saline control | | | | |
| Mean | 136.1 | 158.4 | 141.0 | 169.0 |
| Standard deviation | 40.54 | 33.11 | 15.49 | 6.53 |
| $N^1$ | 7 | 7 | 7 | 7 |
| Group 2 - HPBCD | | | | |
| Mean | 68.7 | 81.4 | 100.6 | 87.4 |
| Standard deviation | 23.70 | 20.66 | 14.48 | 31.78 |
| $N^1$ | 7 | 7 | 7 | 7 |

[1]N - number of days in the study week.

TABLE XV

Hematology Data

| | Males Pre-study control | | Males Post study values | | Females Pre-study control | | Females Post study values | |
|---|---|---|---|---|---|---|---|---|
| Dose: | 0 mg/kg | 200 mg/kg | 0 mg/kg | 200 mg/kg | 0 mg/kg | 200 mg/kg | 0 mg/kg | 200 mg/kg |
| Blood component | | | | | | | | |

TABLE XV-continued

Hematology Data

| | Males | | | | Females | | | |
|---|---|---|---|---|---|---|---|---|
| | Pre-study control | | Post study values | | Pre-study control | | Post study values | |
| Dose: | 0 mg/kg | 200 mg/kg | 0 mg/kg | 200 mg/kg | 0 mg/kg | 200 mg/kg | 0 mg/kg | 200 mg/kg |
| Red blood cell ($\times 10^6/mm^3$) | 5.48 | 7.00 | 5.50 | 6.83 | 6.61 | 5.68 | 6.31 | 5.27 |
| Hemoglobin (G/DL) | 11.60 | 12.40 | 11.20 | 11.90 | 12.60 | 10.90 | 12.10 | 10.00 |
| Hematocrit (%) | 39.90 | 42.90 | 39.10 | 40.20 | 42.20 | 37.60 | 39.90 | 33.40 |
| Mean corpuscle volume (FL) | 73.00 | 61.00 | 70.00 | 59.00 | 64.00 | 66.00 | 63.00 | 63.00 |
| Mean corpuscle hemoglobin (pg) | 21.20 | 17.70 | 20.10 | 17.40 | 19.10 | 19.20 | 19.20 | 19.00 |
| Mean corpuscle hemoglobin concentrate (%) | 29.10 | 28.90 | 28.60 | 29.60 | 29.90 | 29.00 | 30.30 | 29.90 |
| Platelet count ($\times 10^3/mm^3$) | 294.00 | 473.00 | 398.00 | 574.00 | 515.00 | 369.00 | 692.00 | 372.00 |
| Normal blood cells (/100 white blood cells) | 0.00 | 0.00 | 0.00 | 0.00 | 0.00 | 0.00 | 0.00 | 0.00 |
| White blood cells ($\times 10^3 mm^3$) | 14.50 | 11.30 | 13.30 | 9.50 | 7.70 | 6.90 | 5.50 | 3.70 |
| Segmented neutrophils ($\times 10^3/mm^3$) | 3.34 | 0.90 | 4.12 | 0.76 | 1.62 | 3.38 | 2.36 | 1.11 |
| Lymphocytes ($\times 10^3/mm^3$) | 11.02 | 10.17 | 8.78 | 8.55 | 5.78 | 3.10 | 2.92 | 2.48 |
| Monocytes ($\times 10^3/mm^3$) | 0.14 | 0.11 | 0.27 | 0.10 | 0.00 | 0.07 | 0.11 | 0.07 |
| Eosinophils ($\times 10^3/mm^3$) | 0.00 | 0.11 | 0.13 | 0.10 | 0.31 | 0.34 | 0.11 | 0.04 |
| Basophils ($\times 10^3/mm^3$) | 0.00 | 0.00 | 0.00 | 0.00 | 0.00 | 0.00 | 0.00 | 0.00 |
| Immature neutrophils ($\times 10^3 mm^3$) | 0.00 | 0.00 | 0.00 | 0.00 | 0.00 | 0.00 | 0.00 | 0.00 |
| Prothrombin time (sec.) | 10.40 | 9.90 | 10.40 | 9.90 | 9.40 | 9.40 | 9.90 | 9.80 |
| Partial thromboplastin time | 24.90 | 24.40 | 23.90 | 23.40 | 22.30 | 23.40 | 9.80 | 25.40 |

TABLE XVI

Hematology Data

| | Males | | | | Females | | | |
|---|---|---|---|---|---|---|---|---|
| | Pre-study control | | Post study values | | Pre-study control | | Post study values | |
| Dose: | 0 mg/kg | 200 mg/kg | 0 mg/kg | 200 mg/kg | 0 mg/kg | 200 mg/kg | 0 mg/kg | 200 mg/kg |
| Blood component | | | | | | | | |
| Glucose (mg/dL) | 79.60 | 106.50 | 55.80 | 65.30 | 105.00 | 84.00 | 74.00 | 51.20 |
| Total proteins (G/dL) | 8.00 | 8.80 | 7.10 | 8.00 | 8.20 | 8.40 | 7.80 | 8.10 |
| Albumin (G/dL) | 4.20 | 4.90 | 4.00 | 4.30 | 4.60 | 4.40 | 4.40 | 4.10 |
| Globulin (G/dL) | 3.90 | 3.90 | 3.10 | 3.70 | 3.50 | 4.00 | 3.30 | 4.00 |
| Albumin/Globulin (Ratio) | 1.10 | 1.30 | 1.30 | 1.20 | 1.30 | 1.10 | 1.30 | 1.00 |
| Total bilirubin (mg/dL) | 0.30 | 0.50 | 0.40 | 0.70 | 0.70 | 0.30 | 0.60 | 0.90 |
| Cholesterol (mg/dL) | 128.00 | 192.00 | 114.00 | 156.00 | 148.00 | 122.00 | 165.00 | 135.00 |
| Triglycerides (mg/dL) | 62.00 | 39.00 | 48.00 | 46.00 | 66.00 | 41.00 | 66.00 | 54.00 |
| Aspartate amino transferase (IU/L) | 40.00 | 44.00 | 45.00 | 33.00 | 51.00 | 35.00 | 42.00 | 26.00 |
| Alanine amino transferase (IU/L) | 29.00 | 24.00 | 37.00 | 21.00 | 27.00 | 17.00 | 28.00 | 13.00 |
| Alkaline phosphate (IU/L) | 431.00 | 588.00 | 549.00 | 560.00 | 381.00 | 279.00 | 345.00 | 270.00 |
| Blood urea nitrogen (mg/dL) | 30.90 | 25.80 | 40.60 | 20.80 | 29.30 | 21.00 | 20.80 | 20.00 |
| Creatinine (mg/dL) | 1.00 | 1.10 | 1.40 | 1.40 | 0.90 | 1.10 | 01.20 | 0.80 |
| Calcium (mg/dL) | 11.40 | 12.10 | 9.30 | 9.80 | 10.90 | 10.00 | 9.70 | 9.30 |
| Ionic phosphate (mg/dL) | 6.40 | 7.70 | 7.80 | 9.30 | 6.80 | 4.80 | 7.80 | 6.30 |
| Sodium (mmol/L) | 148.00 | 148.00 | 145.00 | 148.00 | 147.00 | 143.00 | 149.00 | 149.00 |
| Potassium (mmol/L) | 6.20 | 5.30 | 3.80 | 3.70 | 5.20 | 4.30 | 3.70 | 3.60 |

TABLE XVI-continued

| | Hematology Data | | | | | | | |
|---|---|---|---|---|---|---|---|---|
| | Males | | | | Females | | | |
| | Pre-study control | | Post study values | | Pre-study control | | Post study values | |
| Dose: | 0 mg/kg | 200 mg/kg | 0 mg/kg | 200 mg/kg | 0 mg/kg | 200 mg/kg | 0 mg/kg | 200 mg/kg |
| Chlorine (mmol/L) | 112.00 | 111.00 | 104.00 | 106.00 | 112.00 | 108.00 | 109.00 | 112.00 |

No changes in behavior were observed during the study. No weight changes were observed (TABLE XIII) or changes in daily food consumption (TABLE XIV). No differences were seen in either the hematology values (TABLE XV) or the clinical chemistry values (TABLE XVI). No gross pathological changes and no histopathological findings were observed. It is concluded that in this study, HPBCD administered intravenously was devoid of toxicological effects at a dose of 200 mg/kg.

The ultrafiltration, i.e., the ability of the dialysate to remove fluids, was also studied. The results of this study are presented in TABLE XVII, below.

The procedure for this ultrafiltration study was similar to the procedure utilized in obtaining the data for TABLE II, above, with the exceptions that the dwell time in the rats was 6 hours and the concentration of glucose was 4.25% W/V and three concentrations of HPBCD were used, that is 5, 10 and 15% W/V.

TABLE XVII shows that the 15% HPBCD dialysate actually removed body fluids from the rat. In contrast, the other dialysates are absorped by the rat. This is an especially undesirable affect for the glucose containing dialysate as this results in unwanted caloric input as previously discussed.

TABLE XVII

| | Results of Ultrafiltration Study (mean ± st. dev.) | | | |
|---|---|---|---|---|
| | Dialysate | | | |
| | Glucose | HPBCD | | |
| Concentration (% W/V) | 4.25 | 5 | 10 | 15 |
| Number of specimens | — | 4 | 6 | 4 |
| Osmolality[1] (mOs) | 480 | 290 | 340 | — |
| Volume in | | | | |
| Per body weight (ml/100 g) | 14.94 ± 0.12 | 14.96 ± 0.1 | 14.99 ± 0.10 | 14.92 ± 0.03 |
| Volume out | | | | |
| Per body weight (ml/100 g) | 12.20 + 1.23 | 10.88 ± 1.12 | 12.43 ± 0.79 | 16.41 ± 0.94 |
| Difference[2] (ml/100 g) | −2.7 ± 1.4 | −4.08 ± 1.0 | −2.56 ± 0.8 | +1.48 ± 0.48 |
| Percent change[2] | −18.0 | −23.5 | −16.7 | +10.0 |

[1]Natural physical osmolality is in the range of about 290 to about 300.
[2]A negative (−) value indicates a loss of dialysate to the body. A positive (+) value indicates removal of body fluid from the body.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

I claim:

1. An aqueous composition suitable for peritoneal dialysis and comprising:
   hydroxypropyl-beta-cyclodextrin in an amount in the range of about 5 to about 35 g/dl;
   sodium in an amount in the range of about 110 to about 150 mEq/l;
   potassium in an amount in the range of about 0 to about 5 mEq/l;
   calcium in an amount in the range of about 0 to about 6 mEq/l;
   magnesium in an amount in the range of about 0 to about 4 mEq/l; and
   alkali equivalent in an amount in the range of about 35 to about 40 mEq/l.

2. The aqueous composition in accordance with claim 1 wherein the hydroxypropyl-beta-cyclodextrin has a degree of substitution of about 5 to about 7 and is present in an amount in the range of about 7.5 to about 25 g/dl.

3. A method for peritoneal dialysis which comprises the steps of:
   providing an aqueous dialysate containing:
   hydroxypropyl-beta-cyclodextrin in an amount in the range of about 5 to about 35 g/dl;
   sodium in an amount in the range of about 110 to about 150 mEq/l;
   potassium in an amount in the range of about 0 to about 5 mEq/l;
   calcium in an amount in the range of about 0 to about 6 mEq/l;
   magnesium in an amount in the range of about 0 to about 4 mEq/l; and
   alkali equivalent in an amount in the range of about 35 to about 40 mEq/l.
   introducing an aliquot of said dialysate into the peritoneal cavity of a patient in need of dialysis;
   maintaining the introduced dialysate in the peritoneal cavity for a time period sufficient for toxins present to enter the dialysate; and
   thereafter removing from the peritoneal cavity a dialysate aliquot having an increased toxin content.

4. A substantially glucose-free dialysate composition suitable for peritoneal dialysis and comprising an aqueous dialysis solution containing hydroxypropyl-beta-cyclodextrin having a degree of substitution in the range of about 5 to about 7 and present in a concentration of about 5 to about 35 g/dl.

5. The aqueous dialysis solution in accordance with claim 4 wherein hydroxypropyl-beta-cyclodextrin having a degree of substitution of about 5 to about 7 is present in a concentration of about 7.5 to about 25 g/dl.

6. A method for peritoneal dialysis which comprises the steps of:
- providing an aqueous dialysate containing:
  hydroxypropyl-beta-cyclodextrin having a degree of substitution of about 5 to about 7 in a concentration of about 5 to about 35 g/dl;
- introducting an aliquot of said dialysate into the peritoneal cavity of the patient in need of dialysis;
- maintaining the introduced dialysate in the peritoneal cavity for a time period sufficient for toxins and additional water to enter the dialysate; and
- thereafter removing from the peritoneal cavity a dialysate aliquot having an increased toxin and water content.

7. The method for peritoneal dialysis in accordance with claim 6 wherein hydroxypropyl-beta-cyclodextrin is present in an aqueous dialysate in a concentration of about 7.5 to about 25 g/dl.

* * * * *